United States Patent [19]
Rozzell, Jr.

[11] Patent Number: 5,834,261

[45] Date of Patent: Nov. 10, 1998

[54] METHOD FOR THE PRODUCTION OF CHIRAL VICINAL AMINOALCOHOLS

[75] Inventor: J. David Rozzell, Jr., Burbank, Calif.

[73] Assignee: BioCatalytics, Inc., Burbank, Calif.

[21] Appl. No.: 863,900

[22] Filed: May 27, 1997

[51] Int. Cl.$^6$ .............................. C12P 13/00; C12P 41/00
[52] U.S. Cl. ............................................ 435/128; 435/280
[58] Field of Search ...................................... 435/280, 128

[56] References Cited

FOREIGN PATENT DOCUMENTS 01228468   3/1988   Japan .

OTHER PUBLICATIONS

Didier et al., "Chemo–enzymatic synthesis of 1,2–and 1,3–amino alcohols and their use in the enantioselective reduction of acetophenone and anti–acetophenone oxime methyl ether with borane", Tetrahedron 47 (27): 4941–58 (1991).
Gotor, "Enzymic aminolysis, hydrazinolysis and oximolysis reactions", NATO ASI Ser., Ser. C 381 : 199–208 (1992).
Pedrocchi–Fantoni et al., "Chiral amino alcohols from baker's yeast reduction of alpha keto acid derivatives", Gazz. Chim. Ital. 122 (12): 499–502 (1992).
Geissman, T.A., Rearrangements Involving Electron–deficient Nitrogen in Principles of Organic Chemistry (W. H. Freeman & Co., 1962), pp. 674–675.
1992, C. Bull et al in "Biocatalytic Production of Amino Acids and Derivatives", D. Ruzzolard F. Wagner, Eds., pp. 255–256.
1992, "Preparative Biotransformations," S.M. Roberts, Ed. Chapter 2.
1996, A.K. Saksena et al, *"Tetrahedron letters"*, 37 5657–5660.
1948, Tullar, B. F., *J. Am. Chem. Soc.* 70, 2067–2068.
1986, D. Buisson and R. Azerad, *Tetrahedron Letters*, 27, 2631–2634.
1990, S. Servi, *Synthesis* pp. 1–25.
1985, D. Seebach et al, *Organic Synthesis*, 63, pp. 1–9.
1987, D. W. Brooks and K. W. Woods, *J. Org. Chem.*, 52, 2036–2039.
1988, A. Fauve and H. Veschambre, *J. Org. Chem.*, 53, 5215–5219.
1978, M. Bucciarelli et al, *J. Chem. Soc. Chem. Comm.*, pp. 456–457.
1984, K. Kieslich in *Biotransformations*, vol. 6a, Chapter O.
1980, Z. Shaked and G.M. Whitesides, *J. Am. Chem. Soc.* 102, 7104–7105.
1984, J. B. Jones and T. Takemura, *Canadian J. Chem.*, 62, 77–80.
1949, E. S. Willis and J. F. Lane, *Organic Reactions III.*, Chapter 7, pp. 267–306.
1969, P.A.S. Smith, *Trans. N.Y. Acad. Sci*, 31, 504–515.
1973, S. Simons, Jr., *J. Org. Chem*, 38, 414–416.
1976, W.L.F. Armarego et al, *J. Chem. Soc. Perkin Trans.*, I, 2229–2237.
1974, S. Bittner et al., *Tetrahedron Letters*, 23, 1965–1968.
1974, L. Bauer and O. Exner, *Angew. Chem. Int. Edition*, 13 376–384.
1946, P.A.S. Smith, Organic Reactions. III, Chapter 9, pp. 337–338.
1948, J. M. Saunders and R. J. Slocombe, *Chem. Rev.* 43, 203–218.
1971, D. V. Banthorpe in "The Chemistry of the Azido Group", Chapter 7, pp. 397–405.
1980, J. D. Warren and J. B. Press, *Synth. Communications*, 10, 107–110.

*Primary Examiner*—Sandra E. Saucier
*Attorney, Agent, or Firm*—Christie, Parker & Hale, LLP

[57] ABSTRACT

The disclosure describes a method for the preparation of chiral vicinal aminoalcohols in high optical purity. The method combines the stereoselective reduction of the keto group of a β-ketoacid, β-keotester, or derivative with the stereospecific rearrangement of the corresponding amide, hyroxamic acid, or hydrazide to produce chiral vicinal aminoalcohols with control of stereochemistry at both chiral centers.

41 Claims, No Drawings

METHOD FOR THE PRODUCTION OF CHIRAL VICINAL AMINOALCOHOLS

FIELD OF THE INVENTION

This invention relates to a method for the production of chiral vicinal aminoalcohols, and more specifically to the production of chemical compounds bearing both amino and alcohol functional groups on adjacent carbon atoms and which contain one or more chiral centers.

BACKGROUND

Chiral vicinal aminoalcohols are important intermediates in the synthesis of various pharmaceutical products and product candidates, yet the preparation of these compounds remains a significant synthetic challenge to chemists. Gaining control over the stereochemistry of chiral centers at both the alcohol and amine (or in the simplest cases in which only the alcohol- or amine-bearing carbon is chiral, a single chiral center) at reasonable cost is the key to the successful production of these important chemical intermediates.

One example of such an intermediate is found in the compound SCH 56592, described in Tetrahedron Letters 37,5657 (1996) and references therein, hereby incorporated by reference. SCH 56592 is a potent antifungal compound. At the far right side of the molecule as depicted in the reference is found a chiral vicinal aminoalcohol moiety (3S,4S)-3-amino-4-hydroxypentane; this chiral vicinal aminoalcohol is a key part of SCH 56592 and critical to its biological activity. No efficient and cost effective route for its synthesis exists.

There are a number of other examples of important molecules which contain chiral aminoalcohols, including ephedrine, pseudoephedrine, norephedrine, pseudonorephedrine, epinephrine, norepinephrine, isoserinol, isoleucinol, histidinol, 2-aminocyclopentanol, 2-aminocyclohexanol, and many others. Methods for the production of compounds which contain chiral aminoalcohol functionality tend to be specific for a given molecule or small group of related molecules. For example, several routes exist for the production of ephedrine (see, for example Fodor, *Recent Develop. Chem. Nat. Carbon Compounds* 1, 15–160 (1965). However, these methods are not broadly generalizable to many other chiral vicinal aminoalcohols. The enzyme serine hydroxymethyltransferase can catalyze the production of certain chiral vicinal aminoalcohols such as threonine and phenylserine, but only with severe structural limitations; there is an absolute requirement for glycine as a substrate, limiting carbon-1 to being only a carboxyl group. In addition, only certain aldehydes are accepted as substrates to condense with glycine. Furthermore, a mixture of stereoisomers is invariably obtained, making the production and recovery of highly pure chiral vicinal aminoalcohols difficult. (see C. Bull et al. in Biocatalytic *Production of Amino Acids and Derivatives,* D. Rozzell and F. Wagner, Eds., Hanser Publishers, Munich, (1992) pp. 255–256. Often, classical resolution procedures are used due to the absence of any better method, resulting in the loss of 50% or more of the starting material (see, for example Tullar, *J Am. Chem. Soc.* 70, 2067 (1948) which describes the resolution of D,L-epinephrine). A general method for the production of molecules of high optical purity incorporating a chiral vicinal aminoalcohol would facilitate the production of this important class of pharmaceutical intermediates and would be greatly desired.

DETAILED DESCRIPTION OF THE INVENTION

This invention describes an efficient method for the production of chiral vicinal aminoalcohols. An important aspect of this invention is the generality with which this method described herein may be employed to produce a range of chiral vicinal aminoalcohols, both cyclic and acyclic, with the ability to produce any of the 4 possible stereoisomers in high stereochemical purity.

Central to this invention is the novel combination of two steps, each of which proceeds with a well-defined and controllable stereochemical outcome. The first step is the stereoselective reduction of the keto group of a β-ketoacid, β-ketoester, β-ketocarboxamide, β-ketocarboxylic hydroxamic acid, or β-ketocarboxylic hydrazide (and, in the case of the β-ketoester, conversion to the corresponding carboxamide, hydroxamic acid or hydrazide derivative); this reaction provides for control of stereochemistry at both the C-2 and C-3 positions of the β-ketoester or derivative, producing a product having two chiral centers. Stereoselective reduction of the β-ketoacid or derivative is effected by any of a range of microorganisms which are able to reduce carbonyl groups in the presence of a carbon source such as glucose or other carbohydrates. This reaction may be carried out to generate a single diastereomer of the four possibilities in high optical purity, depending on the choice of organism or enzyme for the reduction. The second step is the stereospecific rearrangement of the resulting 2-substituted-3-hydroxycarboxamide, carboxylic hydrazide, or carboxylic hydroxamic acid to the corresponding amino alcohol, resulting in a chiral vicinal alcohol with control of stereochemistry at both chiral centers. This rearrangement occurs with retention of stereochemistry at the carbon bearing the carbonyl group.

The β-ketoacid or its derivative is normally derived from an inexpensive precursor such as ethyl acetoacetate or another acetoacetic ester, or the esters of related β-ketoacids such as a 2-alkyl substituted acetoacetate, cyclohexanone-2-carboxylate, cyclopentanone-2-carboxylate, and the like. Both simple β-ketoesters such as acetoacetate and various 2-alkyl-substituted β-ketoesters may be reduced with control of stereochemistry at both the 2 and 3 positions. Alkyl groups which may be present at the 2-position in the practice of this invention include methyl, ethyl, propyl, isopropyl, butyl, isobutyl, pentyl, isopentyl, hexyl, octyl, vinyl, propargyl, allyl, thiophenyl, thioalkyl, phenyl, benzyl, furoyl, irnidazoyl, carboxymethyl, carboxyethyl, halomethyl, haloethyl, halopropyl, phosphoalkyl, and the like. Conversion of the chiral β-hydroxyester to its amide, hydroxamic acid or hydrazide derivative may be accomplished by straightforward chemical methods well-known to those skilled in the art. For example, heating of a chiral β-hydroxyester with ammonia, hydrazine, or hydroxylamine in ethanol produces the corresponding amide, hydrazide, or hydroxamic acid in high yiel.

Alternatively, conversion of the ester to the amide, hydroxamic acid or hydrazide may be accomplished by enzymatic catalysis. Esterase, lipase, protease, and amidase enzymes, which can catalyze the hydrolysis of esters in the presence of water, will catalyze conversion of the ester to the amide, hydroxamic acid or hydrazide when ammonia, hydroxylamine or hydrazine are present as nucleophiles. The enzymatic conversion has the added advantage that it often can be carried out under very mild conditions (e.g. ambient temperature and pressure). Further, the enzyme can provide additional stereoselection in the conversion of the ester to its corresponding amide, hydroxamic acid or hydrazide derivative, further improving the enantiopurity of the final product in cases where this is desired.

As a further embodiment of this invention, the β-ketoacid or β-ketoester may be first converted into its amide, hydroxamic acid, or hydrazide derivative, and the stereoselective reduction carried out directly on the amide, hydroxamic acid, or hydrazide derivative. For example, acetoacetamide or a 2-substituted acetoacetamide may be subjected to the stereoselective reduction by a microorganism or a dehydrogenase, followed by the Hofmann rearrangemeat on the 2-substituted-3-hydroxybutyramide to give the chiral vicinal aminoalcohol. Similarly, the hydroxamic acid or hydrazide derivatives of a 2-substituted (or unsubstituted) β-ketoacid may be stereoselectively reduced and then converted to the desired chiral vicinal aminoalcohol using the Lossen or Curtius rearrangements, respectively.

Stereoselective reduction may be conveniently carried out using whole cells or isolated enzymes. In the case of whole cells, organisms useful in the practice of this invention are described in Preparative Biotransforrnations (S.M. Roberts, editor), Chapter 2, John Wiley & Sons, Chichester, U.K. (1996)and references therein; D. Buisson and R Azerad, Tetrahedron Lett., (1986) 27, 2631, and references therein; S. Servi, *Synthesis,* 1 (1990) and references therein; D. Seebach et al., *Organic Synthesis* 63, 1 (1985) and references therein; D. W. Brooks and K. W. Woods, *J Org. Citent.* 52, 2036 (1987) and references therein; A. Fauve and H Veschamnbre, *J Org. Chem.* 53, 5215 (1988) and references therein; Bucciarelli et al., *J Cttem. Soc. Citent. Comnt.,* 456 (1978) and references therein; K. Kieslich in *Biotransformations,* Eds. H. J. Rehm and G. R. Reed, volume 6a, VCH, Weinheim (1984) and references therein; all hereby incorporated by reference; and include *Saccharomyces cerevisiae, Geotrichum candidum, Colletorichum gloeosporioides, Rhizopus arrhizus, Aspergillus niger, Mortierella isabellina,* and other microorganisms.

It is also possible to use isolated dehydrogenase enzymes, either as crude, partially purified, or pure preparations in the practice of this invention. Dehydrogenases useful in the practice of this invention may be isolated and purified, if desired, from microorganisms capable of effecting the stereoselective reduction. The purification of the dehydrogenase enzymes may be accomplished by techniques well known to those skilled in the art. Some examples of purification methods for enzymes may be found in *Methods in Enzymology,* 22 (1971) and references therein, hereby incorporated by reference. In the case of isolated enzymes, the nicotinamide cofactor is recycled using any of a number of recycling schemes known in the prior art [See, for example, Preparative *Biotransformations* (S.M. Roberts, editor), 3.1.13.1.6, John Wiley & Sons, Chichester, U.K. (1996) and references therein; Z. Shaked and G. M. Whitesides, *J Am. Chem. Soc.* 102, 7104–5 (1980) and references therein; J B. Jones and T. Takamura, *Can. J Chem.* 62, 77 (1984); all hereby incorporated by reference.] These enzymes may be used in solution or, if desired, as immobilized enzymes in accord with the practice of this invention. A number of methods of immobilization for both whole cells containing enzymes and for isolated enzymes are known in the prior art and may be used in the practice of this invention. One example of an immobilized enzyme system is described by Weetall et al., *Methods in Enzymology* 34, 59–72 (1974) which is hereby incorporated by reference. In this method enzymes may be immobilized on a porous glass or ceramic support which has been activated with glutaraldehyde. Other methods for immobilization of both cells and enzymes which may be used in the practice of this invention are described in *Methods in Enzymology* 44 (1976), K. Mosbach editor, *Immobilization of Enzymes and Cells,* Gordon F. Bickerstaff, ed., Humana Press, Totowa, NJ (1997) and in *Biocatalytic Production of Amino Acids and Derivatives,* D. Rozzell and F. Wagner, Eds., Hanser Publishers, Munich, (1992) pp. 279–319.

The stereospecific rearrangement may be carried out on the carboxamide via the Holmann-type rearrangement [E. S. Wallis and J. F. Lane, *Organic Reactions* III, 267 (1949) and references therein; P. A. S. Smith, *Trans. N.Y. Acad. Sci.* 31, 504 (1969) and references therein; S. Simons, *J. Org Chem.* 38, 414 91973) and references therein; W. L. F. Armarego et al, *J. Chem. Soc. Perkin Trans.* I, 2229 (1976) and references therein; all hereby incorporated by reference]; on the hydroxamic acid via the Lossen rearrangement [S. Bittner et al (*Tet. Lett.* 23, 1965–8 (1974) and references therein; L. Bauer and O. Exner, *Angew. Chem. Int. Ed.* 13, 376 (1974) and references therein; all hereby incorporated by reference]; or on the hydrazide via the Curtius rearrangement [P. A. S. Smith, *Organic Reactions* III, 337 (1946) and references therein; J. H. Saunders and R. I. Slocombe, *Chem. Rev.* 43, 205 (1948) and references therein; D. V. Banthorpe in *The Chemistry of the Azido Group,* S. Patai Ed., Interscience, New York, 1971, pp. 397–405 and references therein; J. D. Warren and J. D. Press, *Synth. Comm.* 10, 107 (1980) and references therein; all hereby incorporated by reference].

The application of this method to produce the key component of SCH 56592 yields the desired product from the following simple and inexpensive chemical building blocks: ethyl 2-ethylacetoacetate (produced from ethyl acetoacetate and ethyl bromide), ammonia (or hydroxylamine or hydrazine), and bromine (or benzoyl chloride or sodium nitrite). The following is illustrative of the straightforward application of this invention.

Ethyl 2-ethylacetoacetate is added to a culture of *Rhizopus arrhizus* ATCC 11145 which had been cultivated on glucose as a carbon source. After 48 hours of agitation, the culture broth is filtered, extracted with ethyl acetate, and evaporated to leave 2S,3S-ethyl 2-ethyl-3-hydroxybutyrate as a yellowish oil. This product is warmed with hydrazine in ethanol, and the resulting hydrazide is isolated and treated with sodium nitrite in 5% sulfuric acid to produce 2S,3S-2-amino-3-hydroxypentane via the Curtius rearrangement.

In cases where the alcohol is the only chiral center, the sequence is similarly effective, maintaining complete control over the chirality of the alcohol after stereospecific reduction through the rearrangement of the amide, hydrazide, or hydroxamic acid.

The invention will now be further illustrated by the following examples which are given here for illustrative purposes only and are not intended to limit the scope of the invention.

EXAMPLE 1

Production of ethyl (2R,3S)-2-ethyl-3-hydroxybutyrate

Twenty grams of bakers' yeast (Sigma Chemical Company, *Saccharomyces cerevisiae,* type II) was suspended in a solution of 30 grams of sucrose in water in a conical flask, and the mixture was placed in an orbital shaker chamber maintained at 220 rpm and 30° C. for 30 minutes to initiate fermentation. Two grams of ethyl 2-ethyl acetoacetate was dissolved in 2 ml of 95% ethanol, the resulting solution was added to the fermenting yeast, and shaking was resumed. The reaction was followed by TLC (staining with phosphomolybdic acid in ethanolic sulfuric acid) to monitor the consumption of starting material and the production of product alcohol. After approximately 48 hours the reaction was judged complete, and the reaction was terminated by removing the flask from the shaker and adding 20–30 grams of Celite to the reaction mixture. The resulting suspension was suction filtered through a pad of Celite, and the clear yellow filtrate was extracted with ethyl acetate (4×200 ml). The extracts were combined, dried over $MgSO_4$, filtered, and rotary evaporated to leave 1.6 grams of a yellowish oil containing ethyl (2R,3S)-2-methyl-3-hydroxybutyrate as the major product (80%) and ethyl (2S,3S)-2-methyl-3-hydroxybutyrate (20%) as the minor product as judged by chiral chromatography.

EXAMPLE 2

Production of octyl (2R,3S)-2-ethyl-3-hydroxybutyrate

Twenty grams of bakers' yeast (Sigma Chemical Company, type II) was suspended in an aqueous solution containing 30 grams of sucrose in a conical flask, and the mixture was placed on an orbital shaker (220 rpm) at 30° C. for 30 minutes to initiate fermentation. Two grams of octyl 2-ethyl acetoacetate was dissolved in 2 ml of 95% ethanol, the resulting solution was added to the fermenting yeast, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1.8 grams of octyl (2R,3S)-2-ethyl-3-hydroxybutyrate as a yellowish oil (>96% enantiomeric excess as judged by chiral chromatography).

EXAMPLE 3

Production of (2R,3 S)-ethyl 2-allyl-3-hydroxybutyrate

Twenty grams of bakers' yeast (Sigma Chemical Company, type II) was suspended in an aqueous solution containing 30 grams of sucrose in a conical flask, and the mixture was placed on an orbital shaker (220 rpm) at 30° C. for 30 minutes to initiate fermentation. Two grams of ethyl 20-methyl acetoacetate was dissolved in 2 ml of 95% ethanol, the resulting solution was added to the fermenting yeast, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1.6 grams of a yellow oil containing (2R,3S)-2-ethyl-3-hydroxybutyrate as the major product (75%) and (2S,3S)-2-ethyl-3-hydroxybutyrate (25%) as the minor product as judged by chiral chromatography.

EXAMPLE 4

Production of ethyl (2S,3S)-2-ethyl-3-hydroxybutyrate

*Colletotrichum gloeosporioides* (MMP 3233) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KCl (0.5 gram) with rotary shaking at 25° C. Two grams of ethyl 2-ethyl acetoacetate was dissolved in 2 ml of 95% ethanol, the resulting solution was added to the culture, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1.7 grams of (2S,3S)-2-ethyl-3-hydroxybutyrate as a yellow oil. The chiral purity of the product was greater than 98% as judged by chiral chromatography.

EXAMPLE 5

Alternative production of ethyl (2S,3S)-2-ethyl-3-hydroxybutyrate

*Rhizopus arrhizus* (ATCC 11145) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KCl (0.5 gram) with rotary shaking at 25° C. Two grams of ethyl 2-ethyl acetoacetate was dissolved in 2 ml of 95% ethanol, the resulting solution was added to the culture, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1.6 grams of (2S,3S)-2-ethyl-3-hydroxybutyrate as a yellow oil. The chiral purity of the product was shown to be greater than 98% as judged by chiral chromatography.

EXAMPLE 6

Alternative production of ethyl (2S,3S)-2-ethyl-3-hydroxybutyrate

Two grams of ethyl 2-ethyl acetoacetate was dissolved in 2 ml of 95% ethanol, and the resulting solution was added to a solution of alcohol dehydrogenase (500 units from *Rhizopus arrhizus* (ATCC 11145) containing potassium phosphate buffer, 100 mM, pH 7.0. NAD+(100 mg) was added to the solution along with 1 gram of sodium formate and 100 units of formate dehydrogenase (Boehringer Mannhelm). for recycling of the NAD+cofactor. The reaction was followed by TLC (staining with anisaldehyde) to monitor the consumption of starting material and the production of product alcohol. After approximately 48 hours the reaction was judged complete, and the reaction was terminated by removing from the shaker. The resulting solution was extracted with ethyl acetate (4×200 ml). The extracts were combined, dried over MgSO$_4$, filtered, and rotary evaporated to leave 1.8 grams of (2S,3S)-2-ethyl-3-hydroxybutyrate as a light yellow oil. The chiral purity of the product was greater than 99% as judged by chiral chromatography.

EXAMPLE 7

Production of (1S,2R)-ethyl 2-hydroxycyclopentanecarboxylate

Twenty-five grams of bakers' yeast (*Saccharomyces cerevisiae*, Sigma Chemical Company, type II) was suspended in 100 ml of sterilized tap water in a conical flask, and the mixture was placed on an orbital shaker (220 rpm) at 30° C. for 1 hour to activate the yeast. One gram of ethyl 2-oxocyclopentanecarboxylate was added, shaking was resumed, and progress of the reaction was monitored by TLC (staining with anisaldehyde). After approximately 100 hours the reaction was judged complete, and the reaction was terminated by removing from the shaker and adding 20–30 grams of Celite. The resulting suspension was suction filtered through a pad of Celite and the clear yellow filtrate was extracted with diethyl ether (4×100 ml). The extracts were combined, dried over MgSO$_4$, filtered, and rotary evaporated to leave 0.7 grams of octyl (1R,2S)-ethyl 2-hydroxycyclopentanecarboxlate as a yellowish oil (70% yield).

EXAMPLE 8

Production of (1R,2S)-ethyl 2-hydroxycyclohexanecarboxylate

Twenty-five grams of bakers' yeast (*Saccharomyces cerevisiae*, Sigma Chemical Company, type II) was suspended in 100 m of sterilized tap water in a conical flask, and the mixture was placed on an orbital shaker (220 rpm) at 30° C. for 1 hour to activate the yeast. One gram of ethyl 2-oxocyclohexanecarboxylate was added, shaking was resumed, and progress of the reaction was monitored by TLC (staining with anisaldehyde). After approximately 100 hours the reaction was judged complete, and the reaction was terminated by removing from the shaker and adding 20–30 grams of Celite. The resulting suspension was suction filtered through a pad of Celite and the clear yellow filtrate was extracted with diethyl ether (4×100 ml). The extracts were combined, dried over MgSO$_4$, filtered, and rotary evaporated to leave 0.6 grams of octyl (1R,2S)-ethyl 2-hydroxycyclohexanecarboxylate as a yellowish oil (60% yield).

EXAMPLE 9

Production of (1S,2S)-ethyl 2-hydroxycyclopentanecarboxylate

*Geotrichum candidum* (ATCC 34614) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KCl (0.5 gram) with rotary shaking at 25° C. Two grams of ethyl 2-oxocyclopentanecarboxylate was dissolved in 2 ml of 95% ethanol, the resulting solution was added to the culture, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over MgSO$_4$, filtered, and rotary evaporated to leave 1.5 grams of (1S,2S)-2-hydroxycyclopentanecarboxylate as a yellow oil. The chiral purity of the product was greater than 99% as judged by chiral chromatography.

EXAMPLE 10

Production of (1S,2S)-ethyl 2-hydroxycyclohexanecarboxylate

*Geotrichum candidum* (ATCC 34614) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KCl (0.5 gram) with rotary shaking at 25° C. Two grams of ethyl 2-oxocyclohexanecarboxylate was dissolved in 2 ml of 95% ethanol, the resulting solution was added to the culture, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over MgSO$_4$, filtered, and rotary evaporated to leave 1.4 grams of (1S,2S)-ethyl 2-hydroxycyclohexanecarboxylate as a yellow oil. The chiral purity of the product was greater than 99% as judged by chiral chromatography.

EXAMPLE 11

Production of ethyl 3(S)-hydroxybutyrate

Twenty grams of bakers' yeast (Sigma Chemical Company, type II) was suspended in an aqueous solution containing 30 grams of sucrose in a conical flask, and the mixture was placed on an orbital shaker (220 rpm) at 30° C. for 30 minutes to initiate fermentation. Two grams of ethyl acetoacetate was dissolved in 2 ml of 95% ethanol, the resulting solution was added to the fermenting yeast, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over MgSO4, filtered, and rotary evaporated to leave 1.5 grams of a light yellow oil containing ethyl 3(S)-hydroxybutyrate as the major product as judged by chiral chromatography.

EXAMPLE 12

Production of (R)-ethyl 3-hydroxybutyrate

*Geotrichum candidum* (ATCC 34614) was cultured according to the method of Buisson and Azerad (Tet. Lett.

27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KC1(0.5 gram) with rotary shaking at 25° C. Two grams of ethyl acetoacetate was dissolved in 2 ml of 95% ethanol, the resulting solution was added to the culture, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1.4 grams of (R)-ethyl 3-hydroxybutyrate as a yellow oil.

EXAMPLE 13

Production of (2S,3S)-2 ethyl-3-hydroxybutyramide by microbial reduction of the corresponding 2-ethylacetoacetamide

*Geotrichum candidum* (ATCC 34614) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KCl (0.5 gram) with rotary shaking at 25° C. Two grams of 2-ethyl-3-ketobutyramide was dissolved in 2 ml of 95% ethanol, the resulting solution was added to the culture, and shaking was resumed. The reaction was followed by TLC (staining with anisaldehyde) to monitor the consumption of starting material and the production of product alcohol. After 48–72 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1 gram of (2S,3S)-2 ethyl-3-hydroxybutyramide as a yellowish solid.

EXAMPLE 14

Production of S-3 hydroxybutyramide

Twenty grams of bakers' yeast (Sigma Chemical Company, type II) was suspended in an aqueous solution containing 30 grams of sucrose in a conical flask, and the mixture was placed on an orbital shaker (220 rpm) at 30° C. for 30 minutes to initiate fermentation. Two grams of acetoacetamide was dissolved in 2 ml of 95% ethanol, the resulting solution was added to the fermenting yeast, and shaking was resumed. The reaction was followed by TLC (staining with anisaldehyde) to monitor the consumption of starting material and the production of product alcohol. After approximately 48 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1.4 grams of (s)-3-hydroxybutyramide as a light yellow solid.

EXAMPLE 15

Production of the hydroxamic acid of (2S,3S)-2 ethyl-3-hydroxybutyrate (2S,3S)-Ethyl 2 ethyl-3-hydroxybutyrate (1 gram) was dissolved in 5 ml of absolute ethanol, followed by the addition of 0.5 gram of hydroxylamine. The solution was heated to reflux, and the progress of the reaction was followed by thin layer chromatography. After the reaction was judged complete, the ethanol was evaporated and the resulting residue redissolved in ethyl acetate. Hydroxylamine was removed by extraction with 1% HCl and the ethyl acetate solution was dried over $MgSO_4$, filtered, and rotary evaporated to leave 0.8 grams of the hydroxamic acid derivative of (2S,3S)-2 ethyl-3-hydroxybutyrate.

EXAMPLE 16

Enzymatic production of the hydroxamic acid of (2S,3S)-2 ethyl-3-hydroxybutyrate (2S,3S)-Ethyl 2 ethyl-3-hydroxybutyrate (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1 % HC1 and the ethyl acetate solution was dried over $MgSO_4$, filtered, and rotary evaporated to leave 0.8 grams of the hydroxamic acid derivative of (2S,3S)-2 ethyl-3-hydroxybutyrate.

EXAMPLE 17

Alternative production of the hydroxamic acid of (2S,3 S)-2 ethyl-3-hydroxybutyrate by microbial reduction of the corresponding hydroxamic acid of 2-ethylacetoacetate

*Geotrichum candidum* (ATCC 34614) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KCl (0.5 gram) with rotary shaking at 25° C. Two grams of 2-ethylacetoacetate hydroxamic acid, produced by the reaction of ethyl acetoacetate with hydroxylamine, was dissolved in 2 ml of 95% ethanol, the resulting solution was added to the culture, and shaking was resumed. The reaction was followed by TLC (staining with anisaldehyde) to monitor the consumption of starting material and the production of product alcohol. After 48–72 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over $MgSO_4$, filtered, and rotary evaporated to leave 1 gram of (2S,3S)-2 ethyl-3-hydroxybutyrate hydroxamic acid as a yellowish solid.

EXAMPLE 18

Conversion of (2S,3S)-ethyl 2-ethyl-3-hydroxybutyrate to the hydrazide derivative (2S,3S)-Ethyl 2 ethyl-3-hydroxybutyrate (1 gram) was dissolved in 5 ml of absolute ethanol, followed by the addition of 0.5 gram of hydrazine. The solution was heated to reflux, and the progress of the reaction was followed by thin layer chromatography. After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (2S,3S)2 ethyl-3-hydroxybutyrate.

EXAMPLE 19

Microbial production of the hydrazide of (2S,3 S)-2 ethyl-3-hydroxybutyrate by stereospecific reduction of 2-ethylacetoacetate hydrazide

*Geotrichum candidum* (ATCC 34614) was cultured according to the method of Buisson and Azerad (Tet. Lett. 27, 2631–2634 (1986), herein incorporated by reference) in one liter of a medium of glucose (30 grams), KH2PO4 (1 gram), K2HPO4 (2 grams), corn steep liquor (10 grams) MgSO4.7H20 (0.5 gram), NaNO3 (2 grams), FeSO4.7H20 (0.02 gram), and KC1(0.5 gram) with rotary shaking at 25° C. Two grams of 2-ethylacetoacetate hydrazide, produced by the reaction of ethyl 2-ethylacetoacetate with hydrazine, was dissolved in 2 ml of 95% ethanol, the resulting solution was added to the culture, and shaking was resumed. The reaction was followed by TLC (staining with anisaldehyde) to monitor the consumption of starting material and the production of product alcohol. After 48–72 hours the reaction was judged complete, and the reaction was terminated by removing from the shaker and adding 20–30 grams of Celite. The resulting suspension was suction filtered through a pad of Celite and the clear yellow filtrate was extracted with ethyl acetate (4×200 ml). The extracts were combined, dried over MgSO$_4$, filtered, and rotary evaporated to leave 1 gram of (2S,3S)-2 ethyl-3-hydroxybutyrate hydrazide as a yellowish solid.

EXAMPLE 20

Conversion of (2S,3S)-ethyl 2-ethyl-3-hydroxybutyrate to the amide derivative (2S,3S)-Ethyl 2 ethyl-3-hydroxybutyrate (1 gram) was dissolved in 5 ml of absolute ethanol, followed by the addition of 0.5 gram of gaseous ammonia. The solution was kept in a stoppered flask, and the progress of the reaction was followed by thin layer chromatography. After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (2S,3S)-2 ethyl-3-hydroxybutyramide.

EXAMPLE 21

Production of (2R,3S)-2-amino-3-hydroxybutane by Hofinann Reaction

Ten grams of (2R,3S)-2-methyl-3 hydroxybutyramide was dissolved in 250 ml of 0.03 M NaOH and added slowly to a solution 25 grams of bromine in 300 ml of 0.03 M NAOH. The mixture was warmed with stirring until the reddish brown color disappeared. The solution was then cooled, extracted with methyl t-butyl ether ×250 ml), and the extracts dried over MgSO$_4$, filtered, and the solvent removed by rotary evaporation. The product (2R,3S)-2-amino-3 hydroxy-butane is isolated as a light yellow oil.

EXAMPLE 22

Production of (2R,3S)-2-amino-3-hydroxybutane by Lossen Rearrangement

Ten grams of (2R,3S)-2-methyl-3 hydroxy-butyrohydroxamic acid is reacted with benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over MgSO$_4$, filtered, and the solvent removed by rotary evaporation. The product (2R,3S)-2-amino-3 hydroxy-butane is isolated as a light yellow oil.

EXAMPLE 23

Production of (3S,4S)-3-amino-4-hydroxypentane by Lossen Rearrangement

Ten grams of (2S,2S)-2-methyl-3-hydroxypentanohydroxamic acid is reacted with benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over MgSO$_4$, filtered, and the solvent removed by rotary evaporation. The product (3S,4S)-3-amino-4-hydroxypentane is isolated as a light yellow oil.

EXAMPLE 24

Production of (3S,4S)-3-amino-4-hydroxypentane by a modified Lossen Rearrangement Ten grams of (2S,3S)-2-methyl-3-hydroxypentanohydroxamic acid is reacted with equimolar amounts of diethyl azodicarboxylate and triphenylphosphine in tetrahydrofuran at room temperature using the procedure of Bittner, Grinberg and Kartoon (Tet. Lett. 23, 1965–8 (1974)). Reaction takes place rapidly to produce the product (3S,4S)-3-amino-4-hydroxypentane. The product is isolated by acidification and extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (3S,4S)-3-amino-4-hydroxypentane is isolated as a light yellow oil.

EXAMPLE 25

Production of (2S,3S)-2-amino-3-hydroxybutane

Five grams of (2S,3S)-2-methyl-3-hydroxybutyrate hydrazide is reacted with a solution of 5 grams of sodium nitrite in 100 ml of 5% H$_2$50$_4$. Reaction takes place rapidly to produce the product (2S,3S)-2-amino-3-hydroxybutane. The product is isolated by acidification and extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (2S,3S)-2-amino-3-hydroxybutane is isolated as a light yellow oil.

What is claimed is:

1. A method for producing a chiral vicinal aminoalcohol comprising:
    (a) contacting a β-ketoester capable of being converted to a chiral vicinal aminoalcohol with (i) a microorganism in the presence of a carbon source or (ii) a dehydrogenase in combination with a nicotinamide cofactor, under conditions sufficient to permit the stereoselective reduction of the keto group to form a chiral β-hydroxyester;
    (b) converting the chiral β-hydroxyester to a corresponding amide, hydroxamic acid, or hydrazide derivative, and (c) exposing the amide, hydroxamic acid, or hydrazide derivative to conditions permitting stereospecific rearrangement to the corresponding chiral vicinal aminoalcohol.

2. The method according to claim 1, wherein the β-ketoester has the formula 1:

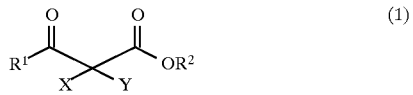

wherein:

X is selected from the group consisting of H, alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted alkyl, thio-substituted alkyl, thio-substituted aryl and heterocyclic;

Y is H;

$R^1$ is selected from the group consisting of alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted aryl, thio-substituted alkyl, thio-substituted aryl, and heterocyclic; or wherein $R^1$, together with X and the carbon atoms to which they are attached, forms a ring; and $R^2$ is selected from the group consisting of alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted aryl, thio-substituted alkyl, thio-substituted aryl, and heterocyclic.

3. The method of claim 1, wherein the microorganism is selected from the group consisting of *Saccharomyces cerevisiae, Geotrichum candidum, Colletorichum gloeosporioides, Rhizopus arrhizus, Aspergillus niger,* and *Mortierella isabellina.*

4. The method of claim 1, wherein the source of the dehydrogenase is a microorganism selected from the group consisting of *Saccharomyces cerevisiae, Geotrichum candidum, Colletorichum gloeosporioides, Rhizopus arrhizus, Aspergillus niger,* and *Mortierella isabellina.*

5. The method of claim 1, wherein the nicotinamide cofactor for the dehydrogenase is recycled.

6. The method of claim 1, wherein the conversion of the ester to the corresponding amide, hydroxamic acid or hydrazide derivative is catalyzed by an esterase, lipase, protease, or amidase.

7. The method of claim 1, further comprising recovering the chiral vicinal aminoalcohol.

8. The method of claim 1, wherein the yield of the β-hydroxyester is at least 60 percent, based on the amount of starting β-ketoester.

9. The method of claim 1, wherein the yield of the β-hydroxyester is at least 80 percent, based on the amount of starting β-ketoester.

10. The method of claim 2, comprising converting the chiral β-hydroxyester of step (a) to a corresponding amide.

11. The method of claim 10, wherein X is selected from the group consisting of alkyl, aryl, benzyl and alkenyl, or wherein X and $R^1$, together with the carbon atoms to which they are attached, form a ring.

12. The method of claim 10, wherein $R^1$ is selected from the group consisting of alkyl, aryl, benzyl and alkenyl, or wherein $R^1$ and X, together with the carbon atoms to which they are attached, form a ring.

13. The method of claim 10, wherein $R^2$ is selected from the group consisting of alkyl, aryl and benzyl.

14. The method of claim 2, comprising converting the chiral β-hydroxyester of step (a) to a corresponding hydroxamic acid.

15. The method of claim 14, wherein X is selected from the group consisting of alkyl, aryl, benzyl and alkenyl, or wherein X and $R^1$, together with the carbon atoms to which they are attached, form a ring.

16. The method of claim 14, wherein $R^1$ is selected from the group consisting of alkyl, aryl, benzyl and alkenyl, or wherein $R^1$ and X, together with the carbon atoms to which they are attached, form a ring.

17. The method of claim 14, wherein $R^2$ is selected from the group consisting of alkyl, aryl and benzyl.

18. The method of claim 2, comprising converting the chiral β-hydroxyester of step (a) to a corresponding hydrazide derivative.

19. The method of claim 18, wherein X is selected from the group consisting of alkyl, aryl, benzyl and alkenyl, or wherein X and $R^1$, together with the carbon atoms to which they are attached, form a ring.

20. The method of claim 18, wherein $R^1$ is selected from the group consisting of alkyl, aryl, benzyl and alkenyl, or wherein $R^1$ and X, together with the carbon atoms to which they are attached, form a ring.

21. The method of claim 18, wherein $R^2$ is selected from the group consisting of alkyl, aryl and benzyl.

22. A method for producing a chiral vicinal aminoalcohol comprising:

a) contacting a β-ketoamide capable of being converted to a chiral vicinal amino alcohol, a β-ketohydroxamic acid capable of being converted to a chiral vicinal amino alcohol, or a β-ketohydrazide capable of being converted to a chiral vicinal amino alcohol with (i) a microorganism in the presence of (i) a carbon source or (ii) a dehydrogenase in combination with a nicotinamide cofactor, under conditions sufficient for stereoselective reduction of the keto group to form a β-hydroxyamide, β-hydroxyhydroxamic acid, or β-hydroxyhydrazide; and (b) exposing the β-hydroxyamide, β-hydroxyhydroxamic acid, or β-hydroxyhydrazide to conditions sufficient to permit stereospecific rearrangement to the corresponding chiral vicinal aminoalcohol.

23. The method according to claim 22, wherein the β-ketoamide has the formula 2, the β-ketohydroxamic acid has the formula 3, and the β-ketohydrazide has the formula 4:

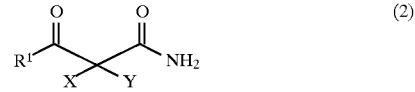

-continued

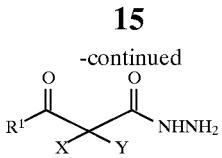
(4)

wherein:
X is selected from the group consisting of H, alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted alkyl, thio-substituted alkyl, thio-substituted aryl and heterocyclic;

Y is H; and $R^1$ is selected from the group consisting of alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted aryl, thio-substituted alkyl, thio-substituted aryl, and heterocyclic; or wherein $R^1$, together with X and the carbon atoms to which they are attached, forms a ring.

24. The method of claim 22, wherein the microorganism is selected from the group consisting of *Saccharomyces cerevisiae, Geotrichum candidum, Colletorichum gloeosporioides, Rhizopus arrhizus, Aspergillus niger,* and *Mortierella isabellina*.

25. The method of claim 22, wherein the source of the dehydrogenase is a microorganism selected from the group consisting of *Saccharomyces cerevisiae, Geotrichum candidum, Colletorichum gloeosporioides, Rhizopus arrhizus, Aspergillus niger,* and *Mortierella isabellina*.

26. The method of claim 22, wherein the nicotinamide cofactor for the dehydrogenase is recycled.

27. The method of claim 22, further comprising recovering the chiral vicinal aminoalcohol.

28. The method of claim 22, wherein yield of the β-hydroxyamide, β-hydroxyhydroxamic acid, or β-hydroxyhydrazide is at least 50 percent, based on the amount of starting β-ketoamide, β-ketohydroxamic acid, or β-ketohydrazide, respectively.

29. The method of claim 22, wherein yield of the β-hydroxyamide is at least 70 percent, based on the amount of starting β-ketoamide.

30. The method of claim 23, comprising contacting a β-ketoamide of formula 2 with a microorganism in the presence of a carbon source or a dehydrogenase in combination with a nicotinamide cofactor under conditions sufficient for stereoselective reduction of the keto group to form a β-hydroxyamide.

31. The method of claim 30, wherein X is selected from the group consisting of alkyl, aryl, benzyl and alkenyl, or wherein X and $R^1$, together with the carbon atoms to which they are attached, form a ring.

32. The method of claim 30, wherein $R^1$ is selected from the group consisting of alkyl, aryl, benzyl and alkenyl, or wherein $R^1$ and X, together with the carbon atoms to which they are attached, form a ring.

33. The method of claim 30, wherein $R^2$ is selected fiom the group consisting of alkyl, aryl and benzyl.

34. The method of claim 23, comprising contacting a β-ketohydroxamic acid of formula 3 with a microorganism in the presence of a carbon source or a dehydrogenase in combination with a nicotinamide cofactor under conditions sufficient for stereoselective reduction of the keto group to form a β-hydroxyhydroxamic acid.

35. The method of claim 34, wherein X is selected from the group consisting of alkyl, aryl, benzyl and alkenyl, or wherein X and $R^1$, together with the carbon atoms to which they are attached, form a ring.

36. The method of claim 34, wherein $R^1$ is selected from the group consisting of alkyl, aryl, benzyl and alkenyl, or wherein $R^1$ and X, together with the carbon atoms to which they are attached, form a ring.

37. The method of claim 34, wherein $R^2$ is selected from the group consisting of alkyl, aryl and benzyl.

38. The method of claim 22 comprising contacting a β-ketohydrazide of formula 4 with a microorganism in the presence of a carbon source or a dehydrogenase in combination with a nicotinamide cofactor under conditions sufficient for stereoselective reduction of the keto group to form a β-hydroxyhydrazide.

39. The method of claim 38, wherein X is selected from the group consisting of alkyl, aryl, benzyl and alkenyl, or wherein X and $R^1$, together with the carbon atoms to which they are attached, form a ring.

40. The method of claim 38, wherein $R^1$ is selected from the group consisting of alkyl, aryl, benzyl and alkenyl, or wherein $R^1$ and X, together with the carbon atoms to which they are attached, form a ring.

41. The method of claim 38, wherein $R^2$ is selected from the group consisting of alkyl, aryl and benzyl.

* * * * *

UNITED STATES PATENT AND TRADEMARK OFFICE
CERTIFICATE OF CORRECTION

PATENT NO.    : 5,834,261
DATED         : November 10, 1998
INVENTOR(S)   : J. David Rozzell, Jr.

It is certified that error appears in the above-identified patent and that said Letters Patent is hereby corrected as shown below:

<u>Title page,</u>
ABSTRACT,
Line 4, change "β-keotester" to -- β-ketoester --.
Line 6, change "hyroxamic" to -- hydroxamic --.

<u>Column 1,</u>
Line 57, change "*JAm. Chem. Soc.*" to -- *J. Am..Chem. Soc.* --.
Line 63, before "DETAILED DESCRIPTION OF THE INVENTION" insert -- SUMMARY OF THE INVENTION
    In one embodiment, the present invention is directed to a method for producing a chiral vicinal aminoalcohol comprising:
    (a) contacting a (β-ketoester capable of being converted to a chiral vicinal aminoalcohol with (i) a microorganism in the presence of a carbon source or (ii) a dehydrogenase in combination with a nicotinamide cofactor, under conditions sufficient to permit the stereoselective reduction of the keto group to form a chiral β-hydroxyester;
    (b) converting the chiral β-hydroxyester to a corresponding amide, hydroxamic acid, or hydrazide derivative, and
    (c) exposing the amide, hydroxamic acid, or hydrazide derivative to conditions permitting stereospecific rearrangement to the corresponding chiral vicinal aminoalcohol.
    The chiral vicinal aminoalcohol can then be recovered. Preferably the yield of the β-hydroxyester is at least 60 percent, based on the amount of starting β-ketoester. More preferably the yield of the β-hydroxyester is at least 80 percent, based on the amount of starting β-ketoester.
    Preferably the β-ketoester has the formula 1:

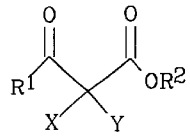

(1)

wherein:
X is selected from the group consisting of H, alkyl, alkenyl, alkynyl, halogen-substituted alkyl, aryl, halogen-substituted aryl, benzyl, halogen-substituted benzyl, thiophenyl, halogen-substituted thiophenyl, hydroxy substituted alkyl, hydroxy-substituted aryl, carboxy-substituted alkyl, carboxy-substituted alkyl, thio-substituted alkyl, thio-substituted aryl and heterocyclic;
Y is H;

UNITED STATES PATENT AND TRADEMARK OFFICE
CERTIFICATE OF CORRECTION

PATENT NO. : 5,834,261
DATED : November 10, 1998
INVENTOR(S) : J. David Rozzell, Jr.

It is certified that error appears in the above-identified patent and that said Letters Patent is hereby corrected as shown below:

$R^1$ is selected from the group consisting of alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted aryl, thio-substituted alkyl, thio-substituted aryl, and heterocyclic; or $R^1$, together with X and the carbon atoms to which they are attached, forms a ring; and $R^2$ is selected from the group consisting of alkyl, alkenyl, alkynyl, halogen-substituted alkyl, aryl, halogen-substituted aryl, benzyl, halogen-substituted benzyl, thiophenyl, halogen-substituted thiophenyl, hydroxy substituted alkyl, hydroxy-substituted aryl, carboxy-substituted alkyl, carboxy-substituted aryl, thio-substituted alkyl, thio-substituted aryl, and heterocyclic.

More preferably X is selected from the group consisting of alkyl, aryl, benzyl and alkenyl, or X and $R^1$, together with the carbon atoms to which they are attached, form a ring. $R^1$ is preferably selected from the group consisting of alkyl, aryl, benzyl and alkenyl, or wherein $R^1$ and X, together with the carbon atoms to which they are attached, form a ring. $R^2$ is preferably selected from the group consisting of alkyl, aryl and benzyl.

In another embodiment, the invention is directed to a method for producing a chiral vicinal aminoalcohol comprising:

a) contacting a β-ketoamide capable of being converted to a chiral vicinal amino alcohol, a β-ketohydroxamic acid capable of being converted to a chiral vicinal amino alcohol, or a β-ketohydrazide capable of being converted a carbon source or (ii) a dehydrogenase in combination with a nicotinamide cofactor, under conditions sufficient for stereoselective reduction of the keto group to form a β-hydroxyamide, β-hydroxyhydroxamic acid, or B-hydroxyhydrazide; and

UNITED STATES PATENT AND TRADEMARK OFFICE
CERTIFICATE OF CORRECTION

PATENT NO. : 5,834,261
DATED : November 10, 1998
INVENTOR(S) : J. David Rozzell, Jr.

Page 3 of 5

It is certified that error appears in the above-identified patent and that said Letters Patent is hereby corrected as shown below:

(b) exposing the β-hydroxyamide, β-hydroxyhydroxamic acid, or β-hydroxyhydrazide to conditions sufficient to permit stereospecific rearrangement to the correspoinding chiral vicinal aminoalcohol. The chiral vicinal aminoalcohol is then recovered. Preferably the yield of the β-hydroxyamide, β-hydroxyhydroxamic acid, or β-hydroxyhydrazide is at least 50 percent, based on the amount of starting β-ketoamide, β-ketohydroxamic acid, or β-ketohydrazide, respectively. More preferably the yield of the β-hydroxyamide is at least 70 percent, based on the amount of starting β-ketoamide.
   Preferably the β-ketoamide has the formula 2, the β-ketohydroxamic acid has the formula 3, and the β-ketohydrazide has the formula 4:

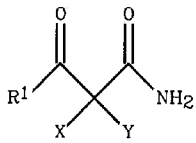 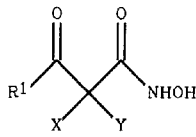 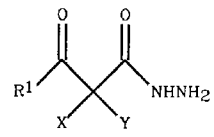

(2)       (3)       (4)

wherein:
   X is selected from the group consisting of H, alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alky,
carboxy-substituted alkyl, thio-substituted alkyl, thio-substituted aryl and heterocyclic;
   Y is H; and
   $R^1$ is selected - from the group consisting of alkyl, alkenyl, alkynyl, halogen-substituted alkyl, aryl, halogen-substituted aryl, benzyl, halogen-substituted benzyl, thiophenyl, halogen-substituted thiophenyl, hydroxy-substituted alkyl, hydroxy-substituted aryl, carboxy-substituted alkyl, carboxy-substituted aryl, thio-substituted alkyl, thio-substituted aryl, and heterocyclic; or $R^1$, together with X and the carbon atoms to which they are attached, forms a ring.
   Preferably X is selected from the group consisting of alkyl, aryl, benzyl and alkenyl, or X and $R^1$, together with the carbon atoms to which they are attached, form a ring. $R^1$ is preferably selected from the group consisting of alkyl, aryl, benzyl and alkenyl, or $R^1$ and X, together with the carbon atoms to which they are attached, form a ring. $R^2$ is preferably selected from the group consisting of alkyl, aryl and benzyl. --

UNITED STATES PATENT AND TRADEMARK OFFICE
CERTIFICATE OF CORRECTION

PATENT NO.   : 5,834,261
DATED        : November 10, 1998
INVENTOR(S)  : J. David Rozzell, Jr.

It is certified that error appears in the above-identified patent and that said Letters Patent is hereby corrected as shown below:

Column 2,
Line 51, change "yiel" to -- yield --.

Column 3,
Line 6, change "rearrangemeat" to -- rearrangement --.
Line 15, change "ofthis" to -- of this --.
Line 22, change "J Org. Citent" to -- J. Org. Citent --
Lines 23 and 24, change "H Veschamnbre" to -- H. Veschambre --
Line 24, change "J Org. Chem." to -- J. Org. Chem. --
Line 25, change "J Cttem. Soc. Citent. Comnt." to, -- J. Cttem. Soc. Citent. Comnt. --.
Lines 48 and 49, change "JAm. Chem. Soc." to -- J. Am. Chem. Soc. --
Line 50, change "Can. J Chem." to -- Can. J. Chem. --

Column 4,
Line 7, change "J. Org Chem." to -- J. Org. Chem. --.
Line 8, change "38, 414 9 1973)" to -- 38, 414-9 (1973)--.

Column 5,
Line 39, change "(2R,3 S)-ethyl" to -- (2R,3S)-ethyl --.

Column 6,
Line 61, after "Mannhelm)" delete the period.

Column 10,
Line 31, change "(2S,3 S)-2" to -- (2S,3S)-2 --.

Column 11,
Line 52, change "Hofinann" to Hofmann --
Line 58, after "ether x250ml" delete the parenthesis., Column 12,
Lines 4 and 18, after "ether x250ml" delete the parenthesis , (both occurrences).
Line 46, change "$H_2 5 0_4$" to -- $H_2 S O_4$ --

Column 13,
Line 17, replace "carboxy-substituted alkyl" (second occurrence) with -- carboxy-substituted aryl --.

UNITED STATES PATENT AND TRADEMARK OFFICE
CERTIFICATE OF CORRECTION

PATENT NO. : 5,834,261
DATED : November 10, 1998
INVENTOR(S) : J. David Rozzell, Jr.

It is certified that error appears in the above-identified patent and that said Letters Patent is hereby corrected as shown below:

Column 14,
Line 43, after "presence of delete "(i)".

Column 15,
Line 12, replace "carboxy-substituted alkyl" (second occurrence) with -- carboxy-substituted aryl --.

Column 16,
Line 13, change "fiom" to -- from --.
Line 32, replace "claim 22" with -- claim 23 --.

Signed and Sealed this

Thirteenth Day of August, 2002

*Attest:*

*Attesting Officer*

JAMES E. ROGAN
*Director of the United States Patent and Trademark Office*